United States Patent
van Ooij et al.

[11] Patent Number: 6,127,320
[45] Date of Patent: Oct. 3, 2000

[54] METHODS AND COMPOSITIONS FOR INCREASING LUBRICITY OF RUBBER SURFACES

[75] Inventors: Wim J. van Ooij, Fairfield, Ohio; Dinesh V. Patwardhan, Rancho Murieta, Calif.

[73] Assignee: University of Cincinnati, Cincinnati, Ohio

[21] Appl. No.: 09/026,376

[22] Filed: Feb. 19, 1998

Related U.S. Application Data
[60] Provisional application No. 60/071,774, Jan. 19, 1998.

[51] Int. Cl.[7] .................................................. C10M 125/26
[52] U.S. Cl. .......................... 508/138; 604/265; 604/289; 524/269
[58] Field of Search ............................. 508/138; 604/265, 604/289; 524/269

[56] References Cited

U.S. PATENT DOCUMENTS

| | | | |
|---|---|---|---|
| 2,980,611 | 4/1961 | Martinek et al. | 252/28 |
| 3,665,041 | 5/1972 | Sianesi et al. | 260/615 A |
| 3,784,471 | 1/1974 | Kaiser | 508/138 |
| 3,968,245 | 7/1976 | Higuchi | 424/330 |
| 4,035,306 | 7/1977 | Lucas et al. | 424/303 |
| 4,036,765 | 7/1977 | Conger et al. | 252/21 |
| 4,086,949 | 5/1978 | Uy | 152/359 |
| 4,523,039 | 6/1985 | Lagow et al. | 568/615 |
| 4,607,675 | 8/1986 | Patitsas et al. | 152/521 |
| 4,803,005 | 2/1989 | Juhlke et al. | 508/590 |
| 4,810,395 | 3/1989 | Levy et al. | 252/28 |
| 4,836,954 | 6/1989 | Tohzuka et al. | 252/54 |
| 4,865,846 | 9/1989 | Kaufman | 424/428 |
| 4,925,583 | 5/1990 | Juhlke et al. | 508/590 |
| 4,925,668 | 5/1990 | Khan et al. | 424/422 |
| 4,942,179 | 7/1990 | Borgarello et al. | 514/659 |
| 4,990,283 | 2/1991 | Visca et al. | 252/309 |
| 4,996,369 | 2/1991 | Kalota et al. | 568/615 |
| 5,073,365 | 12/1991 | Katz et al. | 424/489 |
| 5,100,394 | 3/1992 | Dudar et al. | 604/283 |
| 5,171,234 | 12/1992 | Jepson et al. | 604/283 |
| 5,251,873 | 10/1993 | Atkinson et al. | 251/149.1 |
| 5,312,363 | 5/1994 | Ryan et al. | 604/167 |
| 5,376,359 | 12/1994 | Johnson | 424/46 |
| 5,409,471 | 4/1995 | Atkinson et al. | 604/289 |
| 5,441,488 | 8/1995 | Shimura et al. | 604/265 |
| 5,474,099 | 12/1995 | Boehmer et al. | 137/15 |
| 5,480,914 | 1/1996 | Meadows | 514/743 |
| 5,501,426 | 3/1996 | Atkinson et al. | 251/149.1 |
| 5,512,374 | 4/1996 | Wallace et al. | 428/422 |

(List continued on next page.)

FOREIGN PATENT DOCUMENTS

| | | |
|---|---|---|
| 764537 | 8/1967 | Canada . |
| 1295948 | 4/1983 | Canada . |
| 148482 | 7/1985 | European Pat. Off. . |
| 8700538 | 1/1987 | WIPO . |

OTHER PUBLICATIONS

"CAB–O–SIL® Fumed Silica in Cosmestics and Personal Care Products" http://www.cabot–corp.com/cabosil, 2 pages, Oct. 17, 1997.
"CAB–O–SIL® Fumed Silica in Pharmaceuticals" http://www.cabot–corp.com/cabosil, 2 pages, Oct. 17, 1997.
"CAB–O–SIL® Untreated Fumed Silicas" http://www-.cabot–corp.com/cabosil, 2 pages, Oct. 17, 1997.
"MILSORB–PG™ Colloidal" http://www.milwhite.com/milwhite.com/milsorbpgcolloidal.htm, 2 pages, Oct. 17, 1997.
"Lo–Vel® Flatting Silicas, Hi–Sil® Thixotropic Silicas, Inhibisil™ Non–toxic Anti–corrosion Pigment", http://www.ppg.com/lovel.html, 2 pages, Oct. 17, 1997.
"Typical Properties of Krytox® General Purpose Oils and Greases (1)" http:/www.lubricants.dupont.com/58510.htm, 3 pages, Oct. 17, 1997.

*Primary Examiner*—Jacqueline V. Howard
*Attorney, Agent, or Firm*—Biebel & French

[57] ABSTRACT

Thixotropic, lubricious coatings are provided on the web or surface area surrounding a valve slit or the like in medical, needleless coupling sites. The coating comprises a combination of fluorinated polyalkyl ether and a thixotropic agent such as fumed silica.

28 Claims, 1 Drawing Sheet

U.S. PATENT DOCUMENTS

| | | | |
|---|---|---|---|
| 5,540,661 | 7/1996 | Tomisaka et al. | 604/265 |
| 5,549,576 | 8/1996 | Patterson et al. | 604/247 |
| 5,624,713 | 4/1997 | Ramer | 427/371 |
| 5,636,666 | 6/1997 | Mattern | 141/51 |
| 5,639,810 | 6/1997 | Smith, III et al. | 524/269 |
| 5,653,695 | 8/1997 | Hopkins et al. | 604/265 |
| 5,663,127 | 9/1997 | Flynn et al. | 508/250 |

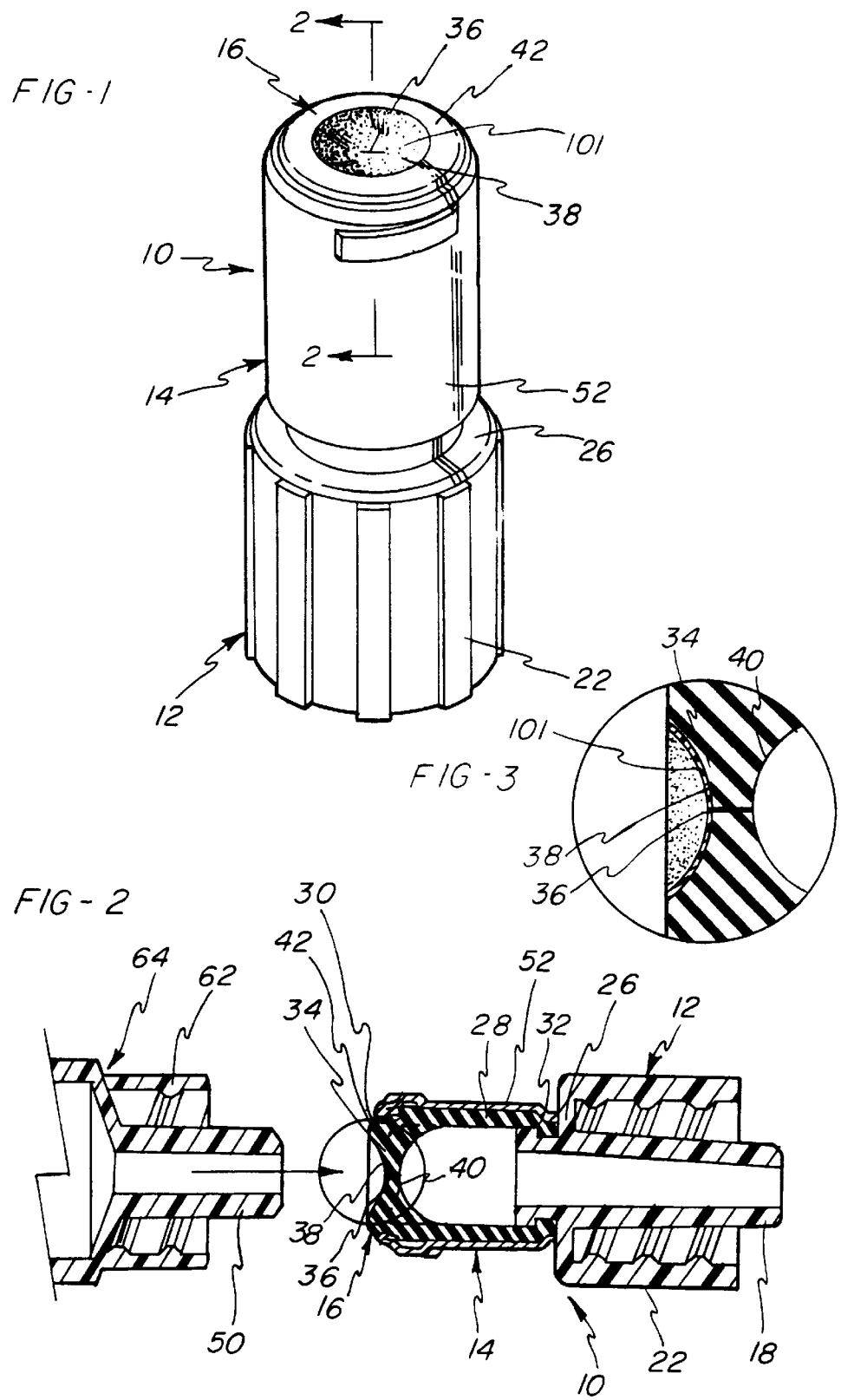

METHODS AND COMPOSITIONS FOR INCREASING LUBRICITY OF RUBBER SURFACES

PRIOR PROVISIONAL APPLICATION

Applicant claims the benefit of the filing date of Provisional Application Ser. No. 60/071,774 filed Jan. 19, 1998.

BACKGROUND OF THE INVENTION

1. Field of the Invention

The present invention pertains to methods and compositions for lubricating rubber surfaces especially those rubber surfaces that are proximate to needleless medical injection sites and valves.

2. Background

In many medical applications, it is necessary to provide a coupling site which includes a rubber valve surface or septum that is to be penetratingly engaged by a sharp hypodermic needle or the like so that fluids such as blood, nutrients or medications can be admitted to a patient's circulatory system through a fluid flow line.

Due to the sharp nature of a needle tip and the ever present fear that infectious disease may be spread via transmission through a needle-pierced or pricked skin area, medical coupling sites and associated fluid feed mechanisms have now been provided that include a coupling site having a rubber valve area surrounding a slit through which a blunt male luer or cannula is inserted. In many designs, after insertion, the luer or cannula is rotated so as to lockingly engage a threaded locking collar or the like. After insertion through the valve slit, the desired fluid is admitted to the fluid flow line that is attached to the coupling site that, in turn, communicates with the circulatory or other body system of the patient.

Usually, the penetrating cannula or male luer is composed of a rigid plastic material, typically polycarbonate. As the cannula is inserted through and rotated in the valve slit, considerable frictional resistance is encountered, especially in those cases where the rubber in the valve surface has been cured via peroxide curing processes. Synthetic rubber, such as peroxide cured polyisoprene has a high frictional coefficient and an effective lubricant is therefore needed at this valve site area since it is highly desirable from an economic perspective to leave the valve and its associated coupling site attached to the patient for multiple fluid admission applications.

Accordingly, an effective method and composition are needed to provide continued lubricity to the valve surface even after numerous cannula penetrations and withdrawals through the valve slit. This requirement dictates that an effective lubricant must remain in place proximate the valve slit over prolonged periods of time.

Additionally, since it is the common practice to sterilize the coupling site and its associated valve surface after each withdrawal and prior to the next cannula penetration with isopropanol, (IPA) the lubricant should be relatively inert to and not miscible with the IPA. Additionally, in many cases, the coupling site will be subjected to irradiation sterilization, so an effective lubricant should also be capable of undergoing such sterilizing methods without significant deterioration.

SUMMARY OF THE INVENTION

We have now developed a new lubricant for rubber surfaces for any application where sliding contact occurs with other materials and where friction should be minimized. This lubricant is essentially a fluorinated polyalkyl ether, such as those commercially available under the trade names, Krytox®—Dupont; Fomblin®—Montedison, or others. While such lubricants reduce the surface energy of the rubber and hence the friction against other materials, they are liquids and hence, they are easily rubbed off the surface. These lubricants do not dissolve in the rubber and therefore, do not affect the rubber's mechanical or other properties. Further, they are chemically stable, non-toxic, and inexpensive.

In this invention, we have modified the lubricant properties of the fluorinated polyalkyl ethers (FPAE) by converting them from a liquid to a thixotropic solid. Such a lubricant will liquefy upon shear and resolidify when the shear is removed. The result is that the lubricant will last much longer than the liquid form, i.e. without thixotropic additives.

The thixotropic additive we found most effective is fumed silica of particle size 1–5 $\mu$m. The optimum concentration is 1.5% by weight The mixture of FPAE and thixotropic agent was homogenized in a high-shear mixture for at least 15 minutes.

The solid lubricant thus obtained is stable for an indefinite period of time, does not deteriorate in conditions of high humidity, and can stand up to prolonged heating at temperatures up to 100° C. without loss of lubricating properties. The Krytox® version that gives optimum performance is Krytox®104, a perfluorinated alkyl ether. The optimum silica content is 1.5% (by weight) of amorphous fumed silica type Cab-O-Sil M-5 (Cabot Corporation). This lubricant behaves like a liquid under shear but becomes a solid instantaneously when the shear is released. Thus, its main advantages are that it behaves like a liquid lubricant but its durability is much improved as compared with the liquid lubricant.

The invention will be further explained in the following detailed description and in the accompanying drawings.

BRIEF DESCRIPTION OF THE DRAWINGS

FIG. 1 is a perspective view of a medical coupling site of the type that may benefit from the instant methods and compositions; and FIG. 2 is a cross sectional view of the coupling site taken along the lines 2—2 in FIG. 1 with a penetrating male luer member positioned adjacent the coupling site prior to its insertion through the valve slit; and FIG. 3 is a magnified cut-a-way view showing the valve site area that is encircled in FIG. 2.

DETAILED DESCRIPTION OF THE PREFERRED EMBODIMENT

Turning to the figures, a typical needleless coupling site is shown that may benefit from the methods and compositions herein described. The coupling site 10 generally includes a support base 12, a retainer 14 supported on the support base and a valve element 16 located within the retainer.

In the preferred embodiment, the support base 12 is formed from a plastic material, the retainer 14 is formed from a plastic material or possibly, but less preferably, metal material such as coated aluminum, and the valve element 16 is formed of an elastomeric material such as an elastomer which conforms to standard medical specifications (e.g. peroxide cured polyisoprene). However, it should be noted that other materials may be used for forming the particular elements of the present medical coupling site 10.

The support base 12 preferably includes a tubular luer taper portion 18 (FIG. 2) defining a longitudinal axis of the coupling site 10. The luer taper portion 18 is surrounded by a threaded locking collar 22 such that the coupling site 10 may be attached to a standard female luer fitting. In addition, an outwardly extending flange portion is attached to an inner end of the luer taper portion 18 extending from an end wall 26 of the collar 22.

The valve member 16 includes a tubular body portion 28 extending substantially parallel to the longitudinal axis and defining a first end 30 and a second end 32 wherein the second end 32 is in contact with the support base 12 adjacent to the end wall 26. The valve element 16 further includes a thin flexible diaphragm 34 extending across the first end 30 of the body portion 16.

The diaphragm 34 includes means defining a slit 36 extending diametrically across the diaphragm 34. In addition, the diaphragm 34 defines opposing first and second sides 38, 40 wherein the first side 38 is formed as a concave surface and the second side 40 is formed as a convex surface. The concave first surface 38 includes a peripheral edge lying in a plane defined by an annular end surface 42 of the body portion 16.

It should be noted that the first surface 38 is provided with a relatively shallow curvature such that the first surface 38 is easily cleaned by wiping of the surface. Also, as a result of forming the diaphragm 34 curved inwardly toward the port base 12, fluid pressure within the site 10 will exert an outwardly directed force on the rounding the slit 36 to compress inwardly, thus biasing the slit closed.

Further, although the second surface 40 is shown having a substantially cylindrical curvature, it should be noted that this surface may also be formed having a spherical or dome-shaped curvature.

Male luer 64 may be in the form of a standard syringe end including a blunt male luer taper 50 and a threaded locking collar 62. In accordance with ANSI and ISO standards and the particular embodiment shown herein for illustration, the male luer taper 50 has an outer diameter of approximately 3.9 mm to 4.0 mm and the threaded locking collar 62 has a minimum inner diameter, as defined by the threaded portion of approximately 7.0 mm to 7.2 mm. In addition, the male luer taper is formed tapering inwardly at an angle of 6°. Thus, the retainer 14 of the coupling site 10 is formed having a maximum outer diameter for the retainer body 52 of approximately 7.0 mm, and the inner wall 48 of the valve element 16 defines a minimum diameter of 4 mm. Additional details pertaining to the structure and operation of the coupling site shown in FIGS. 1–3 may be seen in U.S. Pat. No. 5,251,873 (Atkinson et al.). The disclosure of this patent is incorporated by reference herein. Another needleless coupling site that may benefit from the instant methods and compositions may be seen in U.S. Pat. No. 5,501,426 (Atkinson et al.) also incorporated by reference herein.

In accordance with the present invention, the surface of the valve element 16 surrounding the slit 36 is provided with coating 101 comprising a lubricious thixotropic composition. This composition is composed of a fluorinated ether compound and a thixotropic agent.

As used herein, the phrase "thixotropic composition" is used to denote a composition that becomes fluid or less viscous when disturbed, shaken or subjected to shear. When the internal shearing force is removed, the viscosity returns to approximately its original "at-rest" value.

The fluorinated ether compounds are preferably fluorinated polyalkyl ethers and more preferably are perfluorinated polyalkyl ethers. The perfluorinated polyalkyl ethers that are most preferred are those having $M_n$ values of from around 400 to 20,000 and preferably from about 1800 to about 10,000. Exemplary perfluorinated polyalkyl ethers are described in detail in U.S. Pat. No. 4,990,283 incorporated by reference herein. Commercially available compounds include those sold under the Fomblin®Y, Fomblin®Z or Galden® trademarks by Monteredison or those sold by Daikin. Additional references that describe these compounds and their methods of manufacture include U.S. Pat. No. 4,523,039, European patent 148,482, U.S. Pat. No. 3,665, 041 and WO publication WO 87/00538.

Most preferred are the Kryton® brand perfluorinated polyalkyl ethers commercially available from DuPont. These compounds purportedly have the structure

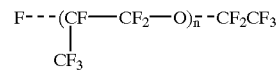

wherein n is about 10 to about 40 (i.e. molecular weights range from about 1804–10,098). Based upon preliminary data available to us, the preferred perfluorinated polyalkyl ethers are available under the Krytox 104 designation. This product purportedly has a $M_n$ of about 2,000.

As to the thixotropic agents that may be used, these can include conventional Theological thickening agents such as clays, silicas, silicates, etc. Most preferred are the silicas and pharmaceutical grade thixotropic clays such as pharmaceutical grade attapulgite available from Milwhite, Inc., Houston, Tex. Additionally, pharmaceutical grade bentonites and modified bentonites may be mentioned. Most preferred are the fumed silicas. These are generally made via high temperature hydrolysis of chlorosilanes in a hydrogen/ oxygen frame. At present, the preferred silica is available from Cabot under the name Cab-O-Sil® M-5 designation. This is classified as an untreated fumed silica having a surface area of about 200 $m^2/g$ and a bulk density of about 2.5 lbs./$ft^3$. Other exemplary silicas that can be mentioned include those commercially available from PPG under the Hi-Sil® marks.

The thixotropic agent is present in the thixotropic lubricating composition in an amount of about 0.5–10 wt % based upon the total weight of the thixotropic composition. More preferably the thixotropic agent is present in an amount of 0.5–5 wt %, with 1–2 wt % even more preferably preferred.

At present, the thixotropic composition preferred for use is

Krytox 104 98.5 wt %

Cab-O-Sil M-5 1.5 wt %

The composition is coated onto the surface of the elastomeric or rubber surface surrounding the slit 36 in a thickness of about 0.1–200 microns. The coating may be applied via a glass rod, dip or brush operation. At present, a glass rod is used as an applicator to coat the elastomeric valve surface. As applied, the thixotropic composition is in a gel or paste-like state. About 0.07 microliters of this composition are evenly coated over the desired valve surface, of the type shown in the drawings.

The compositions of the invention are insoluble in isopropanol, which is commonly used to sterilize the coupling site between cannula insertions. Additionally, the compositions are stable after undergoing 5 M rad. of gamma irradiation and can withstand heats of up to 135° F. without significant degradation.

Preliminary indications show that the lubricating compositions, coated on the valve surfaces of the type shown in the drawings, can withstand in excess of 100 male luer insertions into the slit without resulting in valve failure. In these test, the valve surface is wiped with an IPA solution prior to each insertion so as to simulate actual use conditions.

Additionally, valve surfaces treated in accordance with the invention have passed a 72-hour in-dwell test in which the male luer is nested in the valve slit for a 72-hour period. After this time period, the luer is removed from the so-coated diaphragm with no substantial valve leakage being detected. Valves coated in accordance with the invention also pass a 20 psi back pressure test without deterioration.

Although the invention has been primarily described with reference to the provision of a highly desirable lubricious coating on the rubber valve surfaces associated with a medical, needleless coupling site, the invention is broadly applicable to the lubrication of any rubber surface. The invention is ideally adapted to use as a lubricious coating on polyisoprene surfaces that are or will be in frictional or sliding contact with other surfaces, such as plastic, especially polycarbonate surfaces.

What is claimed is:

1. A method of lubricating a rubber valve surface adapted for frictional contact with a male luer member, said method comprising coating said surface with a lubricious thixotropic composition said lubricious thixotropic composition comprising a fluorinated ether and a thixotropic agent.

2. A method as recited in claim 1 wherein said fluorinated ether comprises a fluorinated polyalkyl ether.

3. A method as recited in claim 2 wherein said fluorinated ether comprises a perfluorinated polyalkyl ether.

4. A method as recited in claim 1 wherein said perfluorinated polyalkyl ether has the structure

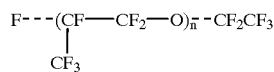

wherein n is about 10 to about 40.

5. A method is recited in claim 1 wherein said thixotropic agent is present in an amount of about 0.5–10 wt % based on the total weight of fluorinated ether and thixotropic agent present in said composition.

6. A method as recited in claim 5 wherein said thixotropic agent is present in an amount of about 0.5–5 wt %.

7. A method as recited in claim 6 wherein said thixotropic agent is present in an amount of about 1.0–2.0 wt %.

8. A method as recited in claim 7 wherein said thixotropic agent is present in an amount of about 1.5 wt %.

9. A method as recited in claim 1 wherein said thixotropic agent comprises a member selected from the group of silicas and clays.

10. A method as recited in claim 9 wherein said thixotropic agent comprises silica.

11. A method as recited in claim 1 wherein said rubber valve surface comprises polyisoprene.

12. A method as recited in claim 1 wherein said step of coating comprises providing a layer of said composition on said surface in a thickness of about 0.1–200 microns in thickness.

13. A method for lubricating an elastomeric valve surface surrounding a slit formed in said surface, said slit adapted for penetration of a cannula therein, said method comprising coating at least a portion of said surface with a lubricious thixotropic composition comprising a perfluorinated polyalkyl ether and a thixotropic agent.

14. A method as recited in claim 13 wherein said perfluorinated polyalkyl ether material has the structure

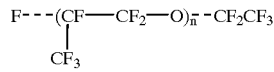

wherein n is about 10 to about 40 and wherein said thixotropic agent comprises fumed silica, said silica being present in an amount of about 0.5–10 wt % based on the total weight of said polyfluorinated polyalkyl ether and said thixotropic agent.

15. A method of lubricating a rubber valve surface comprising coating said surface with a lubricious thixotropic composition comprising a fluorinated ether and a thixotropic agent.

16. A method as recited in claim 15 wherein said fluorinated ether comprises a fluorinated polyalkyl ether.

17. A method as recited in claim 16 wherein said fluorinated ether comprises a perfluorinated polyalkyl ether.

18. A method as recited in claim 17 wherein said perfluorinated polyalkyl ether has the structure

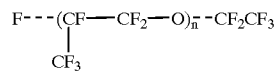

wherein n is about 10 to 40.

19. A method as recited in claim 15 wherein said thixotropic agent is present in an amount of about 0.5–10 wt % based on the total weight of fluorinated ether and thixotropic agent present in said composition.

20. A method as recited in claim 19 wherein said thixotropic agent is present in an amount of about 0.5–5 wt %.

21. A method as recited in claim 20 wherein said thixotropic agent is present in an amount of about 1.0–2.0 wt %.

22. A method as recited in claim 21 wherein said thixotropic agent is present in an amount of about 1.5 wt %.

23. A method as recited in claim 15 wherein said thixotropic agent comprises a member selected from the group of silicas and clays.

24. A method as recited in claim 23 wherein said thixotropic agent comprises silica.

25. A method as recited in claim 15 wherein said rubber valve surface comprises polyisoprene.

26. A method as recited in claim 15 wherein said step of coating comprises providing a layer of said composition on said surface in a thickness of about 0.1–200 microns in thickness.

27. A medical coupling site having a valve member, a thin flexible rubber diaphragm having a slit therein positioned in said valve member, a male luer member adapted for repeated, penetrating insertion through said slit into said valve member, a lubricious thixotropic coating composition proximate said slit for lubricating said slit during said repeated penetrating insertion of said mail luer member therethrough, said coating composition comprising a fluorinated ether and a thixotropic agent, said coating composition being immiscible with isopropanol, whereby said diaphragm and said coating composition are capable of withstanding in excess of 100 of said repeated penetrating insertions without failure of said valve member.

28. Medical coupling site as recited in claim 27 wherein said fluorinated ether comprises a perfluorinated polyalkyl ether having the structure

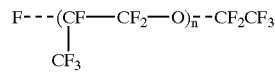

wherein n is from about 10 to about 40 and wherein said thixotropic agent is silica, said thixotropic agent comprising a member selected from the group consisting of silicas and clays, said coating being present on said diaphragm in a thickness of about 0.1–200 microns in thickness.

* * * * *